United States Patent
Vollbrecht et al.

(10) Patent No.: US 9,788,987 B2
(45) Date of Patent: Oct. 17, 2017

(54) ORTHOTIC SYSTEM FOR AN ANKLE JOINT

(75) Inventors: Matthias Vollbrecht, Herzberg am Harz (DE); Gert-Peter Brüggemann, Köln (DE); Andreas Gösele-Koppenburg, Lörrach (DE); Raymond Best, Stuttgart (DE); Andree Ellermann, Ettlingen (DE); Hartmut Semsch, Stuttgart (DE); Kai Dressler, Erfurt (DE); Alfio Albasini, Riazzino (CH); Christian Liebau, Braunschweig (DE)

(73) Assignee: OTTO BOCK HEALTHCARE GMBH, Duderstadt (DE)

( * ) Notice: Subject to any disclaimer, the term of this patent is extended or adjusted under 35 U.S.C. 154(b) by 380 days.

(21) Appl. No.: 12/744,470

(22) PCT Filed: Nov. 14, 2008

(86) PCT No.: PCT/DE2008/001880
§ 371 (c)(1),
(2), (4) Date: Oct. 25, 2010

(87) PCT Pub. No.: WO2009/067982
PCT Pub. Date: Jun. 4, 2009

(65) Prior Publication Data
US 2011/0028877 A1 Feb. 3, 2011

(30) Foreign Application Priority Data

Nov. 28, 2007 (DE) .................. 10 2007 057 578

(51) Int. Cl.
*A61F 5/00* (2006.01)
*A61F 13/00* (2006.01)
*A61F 5/01* (2006.01)

(52) U.S. Cl.
CPC .................. *A61F 5/0111* (2013.01)

(58) Field of Classification Search
CPC ...................................... A61F 5/0111
(Continued)

(56) References Cited

U.S. PATENT DOCUMENTS 3,298,365 A * 1/1967 Lewis .............................. 602/27
4,399,668 A * 8/1983 Williamson ................. 62/457.4
(Continued)

FOREIGN PATENT DOCUMENTS

CN    1082866 A    3/1994
DE    3235929 A1   2/1983
(Continued)

OTHER PUBLICATIONS

PCT International Search Report for PCT International Application No. PCT/DE2008/001880, dated Mar. 20, 2009.

*Primary Examiner* — Kim M Lewis
(74) *Attorney, Agent, or Firm* — Holland & Hart LLP

(57) ABSTRACT

An orthopedic brace system for bracing a joint with a dimensionally stable, flexible base body, which can be placed around the members adjoining the joint and has closure devices by way of which the base body can be fixed to the members adjoining the joint. A dimensionally stable outer frame extending over the joint is removably attached to the base body by way of adjustable fastening members, wherein the outer frame is braced on the members adjoining the joint.

36 Claims, 12 Drawing Sheets

(58) Field of Classification Search
USPC ....... 602/5, 60–65, 23, 27–29; 128/880, 882
See application file for complete search history.

(56) References Cited

U.S. PATENT DOCUMENTS

| | | | |
|---|---|---|---|
| 4,492,225 A | | 1/1985 | Picolet et al. |
| 4,573,456 A | * | 3/1986 | Spann .................... A61F 13/069 |
| | | | 602/27 |
| 5,078,128 A | * | 1/1992 | Grim ..................... A61F 5/0127 |
| | | | 602/23 |
| 5,088,478 A | * | 2/1992 | Grim ................................ 602/27 |
| 5,217,431 A | * | 6/1993 | Toronto et al. ................. 602/27 |
| 5,284,469 A | * | 2/1994 | Jasen .................... A61F 13/126 |
| | | | 128/858 |
| 5,334,135 A | | 8/1994 | Grim et al. |
| 5,370,133 A | * | 12/1994 | Darby et al. .................. 128/882 |
| 5,376,068 A | | 12/1994 | Grifka |
| 5,464,385 A | | 11/1995 | Grim |
| 5,899,872 A | * | 5/1999 | Gilmour .......................... 602/65 |
| 6,428,493 B1 | * | 8/2002 | Pior et al. ....................... 602/10 |
| 6,994,681 B2 | | 2/2006 | Slautterback et al. .......... 602/23 |
| 8,721,578 B2 | * | 5/2014 | Gaylord ............... A61F 5/0102 |
| | | | 602/23 |
| 2003/0050585 A1 | * | 3/2003 | Modglin et al. ................ 602/19 |
| 2004/0019307 A1 | * | 1/2004 | Grim ..................... A61F 5/0195 |
| | | | 602/27 |
| 2005/0145256 A1 | | 7/2005 | Howard et al. |
| 2006/0004311 A1 | * | 1/2006 | Hargrave et al. ................. 602/5 |
| 2006/0217649 A1 | | 9/2006 | Rabe |
| 2008/0004558 A1 | * | 1/2008 | Outred .................. A61F 5/0113 |
| | | | 602/28 |
| 2009/0084390 A1 | * | 4/2009 | Davis ................... A61F 5/0111 |
| | | | 128/882 |

FOREIGN PATENT DOCUMENTS

| | | |
|---|---|---|
| DE | 9407551 U1 | 8/1994 |
| DE | 19650782 A1 | 6/1997 |
| DE | 19638683 A1 | 4/1998 |
| DE | 29908981 U1 | 1/2000 |
| DE | 69718214 T2 | 9/2003 |
| DE | 60005041 T2 | 7/2004 |
| DE | 69915935 T2 | 1/2005 |
| DE | 69728160 T2 | 3/2005 |
| DE | 60022217 T2 | 7/2006 |
| EP | 0567783 A1 | 11/1993 |
| EP | 0876130 B1 | 3/2006 |
| FR | 2697998 A1 * | 5/1994 |

* cited by examiner

ORTHOTIC SYSTEM FOR AN ANKLE JOINT

TECHNICAL FIELD

The invention relates to an orthotic system for an ankle joint for bracing an ankle joint with an inherently stable, flexible base body, which can be placed around the limbs adjoining the ankle joint and which has locking devices by means of which the base body can be fixed against the limbs adjoining the ankle joint. Such a system is particularly suitable for bracing ankle joints with damages to the ligaments. Ligament ruptures or torn ligaments in particular can be treated by such an orthopedic brace system.

BACKGROUND

Bracing devices for joints for the treatment of injuries have been known for a long time. For the treatment of ligament ruptures in the ankle joint, angled splints are attached to the lower leg and the foot by hook-and-loop fasteners in order to fix the joint in a predetermined position.

Furthermore, cuffs are known that are fixed to the limbs adjoining the joint for bracing the joint in a certain movement direction or for blocking such a movement.

EP 0 876 130 B1 has disclosed an orthopedic bracing device in the form of a wrist or ankle joint orthesis, in which a support made of plastic is formed by the injection molding method and it comprises regions of different thicknesses. In order to ensure that it matches the anatomy of the wearer of the bracing device, flexible regions are formed that are thinner than those regions provided for bracing the joint. There are integral locking devices formed on the orthesis for fixing the bracing device to the limbs, and said locking devices are designed as straps with holes, which are pulled through D-rings and hooked into protruding pins. The inside of the bracing device is provided with cushioning. The bracing device itself has hard stabilizing regions.

SUMMARY

The object of the present invention is to provide an orthotic system for an ankle joint, which allows flexible treatment in the case of damages to the supporting apparatus.

According to the invention, this object is achieved by an orthotic system for an ankle joint having the features of claim 1. Advantageous refinements and developments of the invention are listed in the dependent claims.

The orthotic system for an ankle joint according to the invention with an inherently stable, flexible base body, which can be placed around the limbs adjoining the joint and which has locking devices by means of which the base body can be fixed against the limbs adjoining the joint, provides for an inherently stable external frame extending over the joint to be fixed to the base body in a detachable fashion by means of adjustable attachment means and for the external frame to be braced by the limbs adjoining the joint. The external frame without joint device is used to immobilize the joint in a first phase of the treatment in order to obtain the desired therapeutic success. After ligament damage to the ankle joint, the joint should be immobilized in a predetermined position for a period of, for example, one week in order to allow growing together of the ligaments or tightening of the ligaments. After the first phase of the treatment, it is important for the joint to be mobilized in order to accelerate the healing process and prevent stiffening of the joint. For this, the brace system is freed from the external frame and so the orthopedic brace system is worn without external frame during the awake-phase, usually during the day. It is only during the night that the external frame is reapplied in order to prevent involuntary movements and an undesired scope of movement of the joint whilst sleeping.

In order to allow simple application and removal, the inherently stable external frame fixing the joint is fixed to the base body in a detachable fashion by means of adjustable attachment means. The adjustable attachment means allow matching to detumescent joints after injury and so it is easily possible for the system to be adjusted to the healing progress.

A development of the invention provides for the base body to have at least one interlocking element arranged on the outside for fixing at least one part of the external frame, for example a splint, aligned in the longitudinal direction, to be placed against a lower leg. The interlocking element can be designed as a pocket and so this part of the external frame only has to be inserted to enable it, at least in part, to be fixed to the base body. The interlocking element can be sewn on, stuck on, attached by a hook-and-loop fastener or welded on, wherein, in the case of the refinement as a pocket, the external frame is mounted in the interlocking element or in the pocket such that it can be displaced in the longitudinal direction. A part of the external frame can be inserted easily and precisely along a longitudinal extent of a body limb, for example a lower leg, and so only the longitudinal displaceability has to be fixed in order to immobilize the joint. The part of the external frame not inserted into the interlocking element or fixed thereto can be attached to the base body or the limb in a different fashion.

The attachment means for attaching the external frame to the base body are preferably hook-and-loop fasteners such that almost step-less adjustment and matching to the healing progress and the dimensions of the joint to be braced are made possible.

In order to have a further option for treatment, receptacle devices for stiffening elements are formed on or in the base body. These stiffening elements, designed as splints, strengthen the inherent stability of the base body and so, particularly during the second phase of the treatment, a joint can be stabilized during the day after the external frame was removed. Depending on the damage, the stiffening element or stiffening elements can be attached to predetermined receptacle devices or can be inserted therein, particularly in the medial/lateral direction in the case of ankle joint injuries. The receptacle devices for the stiffening elements are preferably designed as pockets and so the stiffening elements can also be easily inserted or removed.

The stiffening elements can be arranged and designed such that they limit or block at least one movement direction of the ankle joint so as not to allow certain movements or ranges of movement, or only allow them in a limited fashion.

Both the external frame and the stiffening elements as well can be made from plastics, composite materials or light metal in order to affect the wearer of the brace system as little as possible.

Provision can be made for a first part of the external frame to extend along the lower leg and a second part of the external frame to extend in the plantar region of the foot so as to be able to hold the foot or part of the foot. Here, the first and the second part of the external frame are preferably arranged at a substantially right angle in order to stabilize the foot and the lower leg in this position with respect to one another and promote healing. In the case of damage to the lateral ligament, the second part, that is to say the foot shell, is aligned in pronation with respect to the lower-leg part. The second part, which can be designed as a foot shell, can preferably be bent in dorsal extension and pronation, while the attachment devices designed as tension belts for fixing the external frame to the base body or separate tension belts limit or block supination and the dorsal flexion. The second part of the external frame, i.e. the foot shell, which can extend as far as below the forefoot, is designed such that it does not cover the first metatarsal head, even if there is further surrounding of the sole of the foot as far as below the forefoot. A further tension belt can be designed as a fixing means, which can be slung around the forefoot.

In the case of an ankle joint bracing, the plantar region of the base body can be formed by two mutually opposing base-body sections, which are coupled to one another by means of at least one connection element, which has hook elements. This affords the possibility of designing the base body from a planar blank and matching it to changing dimensions of the foot or the ankle joint. The connection element can be designed as a separate blank, in particular as a double-sided hook blank, in order to allow as flexible fixing as possible in a refinement of the base body with a layer of fleece on the outside.

Incisions are provided in the region of the Achilles tendon of the base body applied, with adjustment wings being formed by the incisions in order to improve the comfort of wear.

The locking devices are likewise designed as hook elements, in particular as micro-hook elements, in order to allow an almost step-less adjustment. In the process, the locking devices are attached to the base body, formed in particular as belts, and are sewn into through-holes of the base body whilst forming a loop.

In order to increase the comfort of wear, the base body has cushioning in the form of a layer of fleece, and the base body likewise can be completely coated by a layer of fleece on the outside so that the locking devices can be fixed to the base body with nearly no restrictions. The attachment means for attaching the external frame can likewise be arranged thereon, wherein no predetermined attachment points have to be observed in the case of the outside being completely covered by fleece. The type of the attachment and additional stabilization of the limb to the external frame can be brought about individually, and so individual conditions and sensitivities can be taken into account.

The cushioning and the layer of fleece are bonded or welded to one another, in particular, they are laser welded or induction welded to one another. The base body can have cuts within its contour, which in particular have been introduced into the base body in the primary forming method and by a separation method. If the layer of fleece and the cushioning are provided on the base body, these can be welded or bonded to one another through the cuts and thus be attached to the base body. The base body can have a multi-layered design and, in particular, have a mirror-symmetric design.

Material weakenings can be formed in the base body along folding or bending lines in order to allow adjustability to the individual circumstances.

A fixing belt can be attached to the layer of fleece by means of hook elements in order to be able to fix the base body to the limbs.

The attachment means can be designed as inelastic or semi-elastic tension belts, which can be fixed to the base body.

BRIEF DESCRIPTION OF THE DRAWINGS

In the following text, exemplary embodiments of the invention will be explained in more detail on the basis of the attached figures, in which.

DETAILED DESCRIPTION

Figure 1:
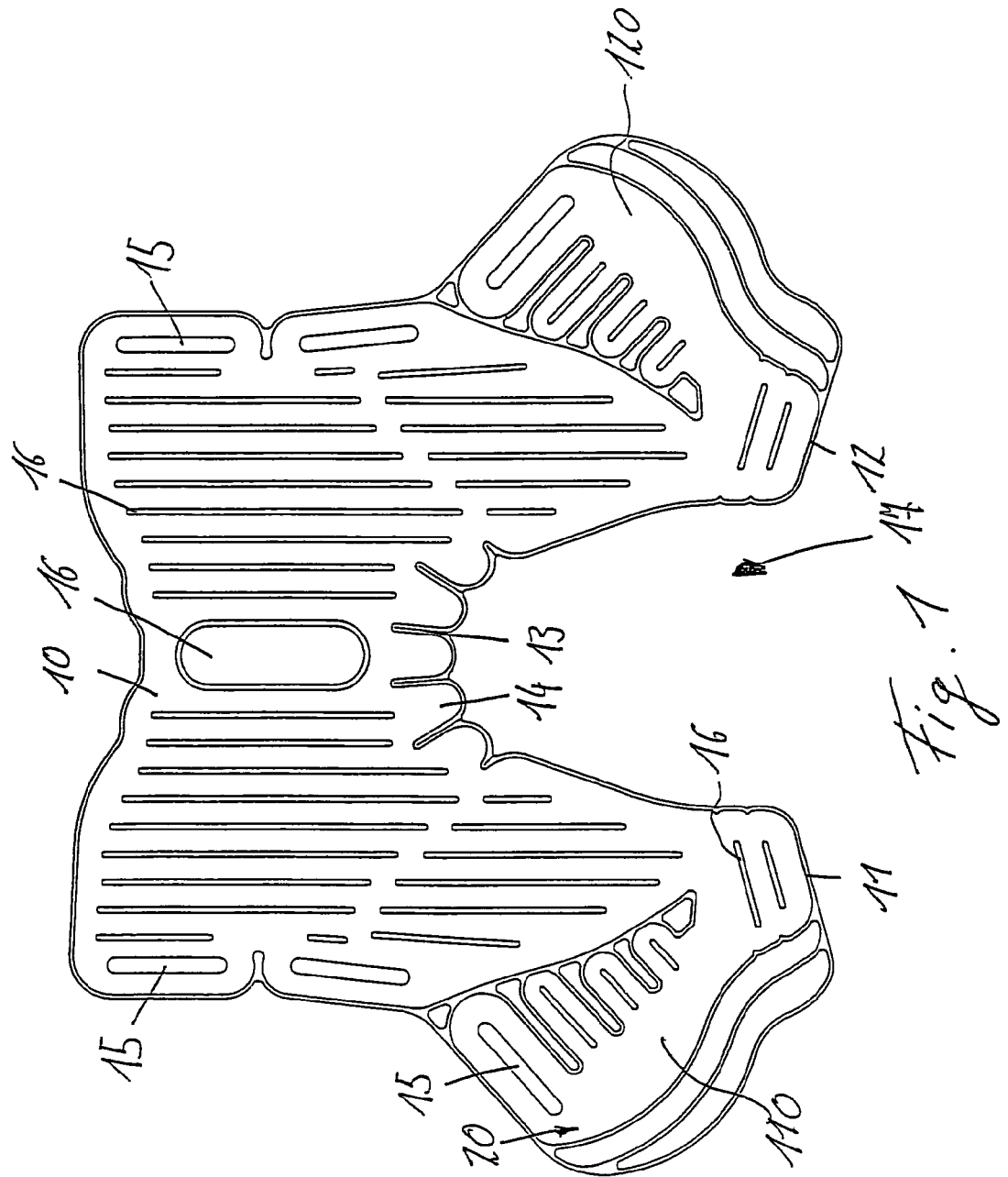
FIG. 1 shows a plan view of a base body blank.

FIG. 1 shows a plan view of a blank of a bracing device 1 with a base body 10, which is entirely coated on the outside by a layer of fleece 20. In the illustrated exemplary embodiment, the base body 10 is provided for use in a bracing device in the form of an ankle joint orthesis and has a mirror-symmetric design. In order to attach the base body 10 to the leg of a user, the base body 10 is applied with its line of reflection being in the region of the Achilles tendon and is folded forward in the direction of the shinbone. Two side regions 110, 120 are wrapped around the foot and mutually opposing base-body sections 11, 12 are situated opposite to one another in the plantar region of the orthesis user in the correspondingly folded over state. In order to ensure increased flexibility in the regions of the folds and for an improved fit of the bracing device to the anatomy of the user, cuts 16 are provided within the base body 10, causing a weakening of the material and thus permitting easier bending. The cuts 16 within the base body 10 made of a planar plastic are covered by the layer of fleece 20 and the cushioning layer situated on the inside (not illustrated), and so a substantially closed surface is formed. This prevents items of clothing or the like from catching thereon. In the region of the cuts 16, both the cushioning layer on the inside and the layer of fleece on the outside are interconnected, preferably bonded or welded, in particular by induction welding.

The layer of fleece 10 and the cushioning layer are likewise welded around the base body 10 and so the base body 10 is completely surrounded by a material or fabric layer. The layer of fleece 20 situated on the outside allows the hook elements to find a counter bearing and so belts or the like can be fixed anywhere on the outside of the base body 10.

Figure 4:
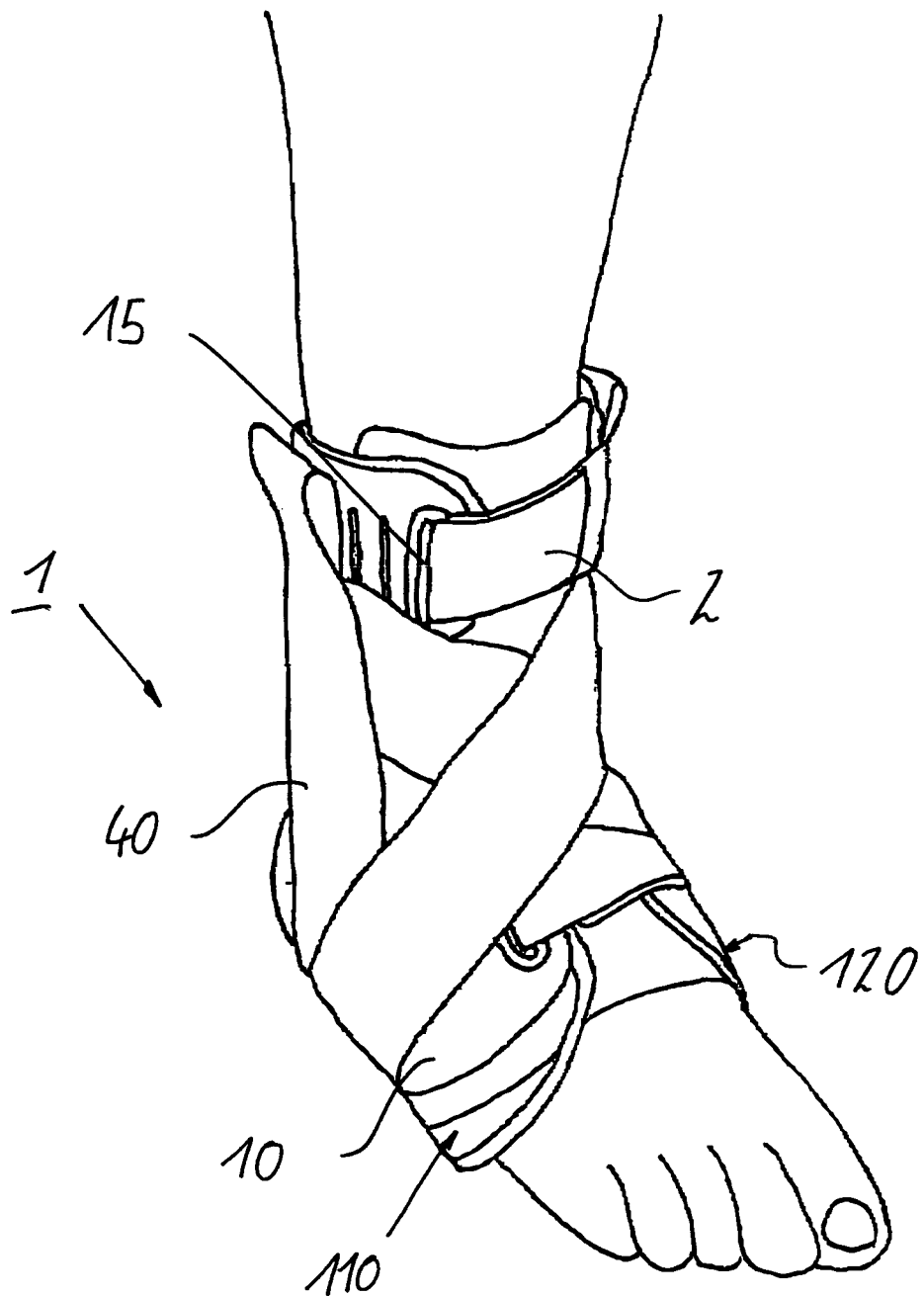
FIG. 4 shows a perspective oblique plan view of an applied base body with a fixing belt.

In order to fix the bracing device to the lower leg or the foot, locking devices illustrated in FIG. 4 are guided through through-holes 15, not provided with a layer of fleece 20 or a cushioning layer, and are sewn to one side. Then the locking devices 2 provided with a hook element are guided through the opposing cut 15 or through-hole and folded back, in order to subsequently be hooked to a region of the layer of fleece 20. Two through-holes 15 arranged above one another are used for fixing the bracing device to the lower leg and a third through-hole 15 in the dorsal region of the foot is used for fixing it on the foot.

A slot-like recess 16 is formed within the base body 10 in the region of the Achilles tendon and said recess eases movement of the foot, particularly a plantar flexion, whereas the mobility of the ankle joint about a pivot axis in the sagittal direction is prevented by the base body 10 and, if need be, by further bracing devices.

Furthermore, there are incisions 13 in the region of the Achilles tendon above a cutout 17 for the heel and these incisions generate adjustment wings 14, which ensure auto-adaptive adjustment and an increased flexibility in the region of the Achilles tendon.

In order to be able to ensure a targeted adjustment of the flexibility of the bracing device, different material strengths are provided in the base body 10, which is preferably of an integral and plate-like design, wherein additional material is provided in regions with increased load. By contrast, material weakenings are provided in those regions that are intended to bend for matching to the anatomy of a user.

Figure 2:
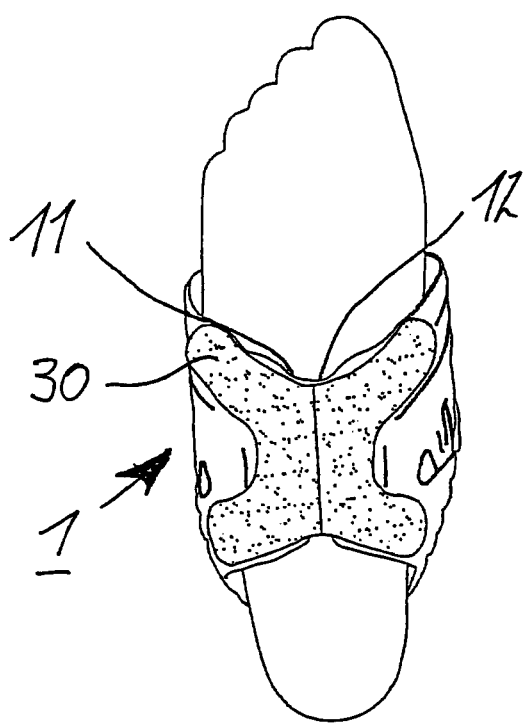
FIG. 2 shows a bottom view of an applied base body.

FIG. 2 shows a bottom view of an applied bracing device in the form of an ankle joint orthesis. In the plantar region, the two base-body sections 11, 12 are aligned opposite one another and are coupled to one another by means of a connection element 30, which has hook elements. The connection element 30 is designed as a separate, integral blank. Here, the connection element 30 preferably consists of a relatively stiff tissue, which is provided with hook devices on at least one side for hooking said element into the outer layer of fleece 20. The relative stiffness of the connection element 30 generates plantar stability of the bracing device 1. On the outside, the connection element 30 can be provided either with a layer of fleece or likewise with a hook layer, in particular a micro-hook layer.

As a result of the separate design of the connection element 30, the base body 10 to be produced in a few standard sizes can easily be matched to different anatomical conditions. Once a single adjustment has been carried out, the connection element 30 can remain in place, and application and removal of the bracing device 1 is brought about by opening and closing the locking devices 2. Moreover, it is possible for the bracing device 1 to be matched to changing anatomies, for example, a gap that may exist between the base-body sections 11, 12 is tightened in the case of detumescent limbs.

Figure 3:
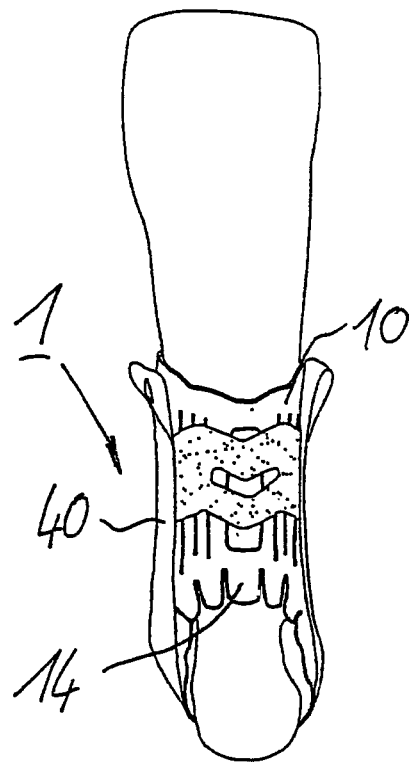
FIG. 3 shows a rear view of an applied base body.

FIG. 3 illustrates a rear view of an applied bracing device 1 with the base body 10. The adjustment wings 14 can clearly be seen. In order to increase the stability, a fixing belt 40 is attached to the layer of fleece 20 on the outside of the base body 10 by means of hook-and-loop fasteners. The fixing belt 40 is flexible but not elastic and so a significant increase in the stiffness is brought about after a single application. The position of the fixing belt 40 or a plurality of fixing belts can be selected without restrictions because the entire surface of the base body 10 is covered by the layer of fleece 20. The illustrated exemplary embodiment of the orthopedic bracing device 1 thus consists of the base body 10 with the cushioning (not visible) and the layer of fleece applied to the outside; a connection element 30 arranged in a plantar direction; and the fixing belt 40 provided with hook elements. If there is no need for additional fixing, the bracing device can also be designed without a fixing belt 40 and it can consist of the base body 10 with the textile layers attached to the outside and the inside, and the connection element 30.

FIG. 4, which shows an applied bracing device 1 in a perspective oblique plan view, shows, in addition to the base body 10 with the foot regions 110, 120 and the though-hole 15 for a locking device 2, the arrangement of the fixing belt 40, which is guided both in a plantar and dorsal fashion and which can be used for fixing the ankle joint, for example after a ligament rupture. As the mobility of the ankle joint increases, the winding can be loosened or the fixing belt 40 can be omitted.

It is also possible for D-rings to be attached to the base body 10 instead of a through-hole 15 in order to attach or guide the locking devices 2.

Figure 5:
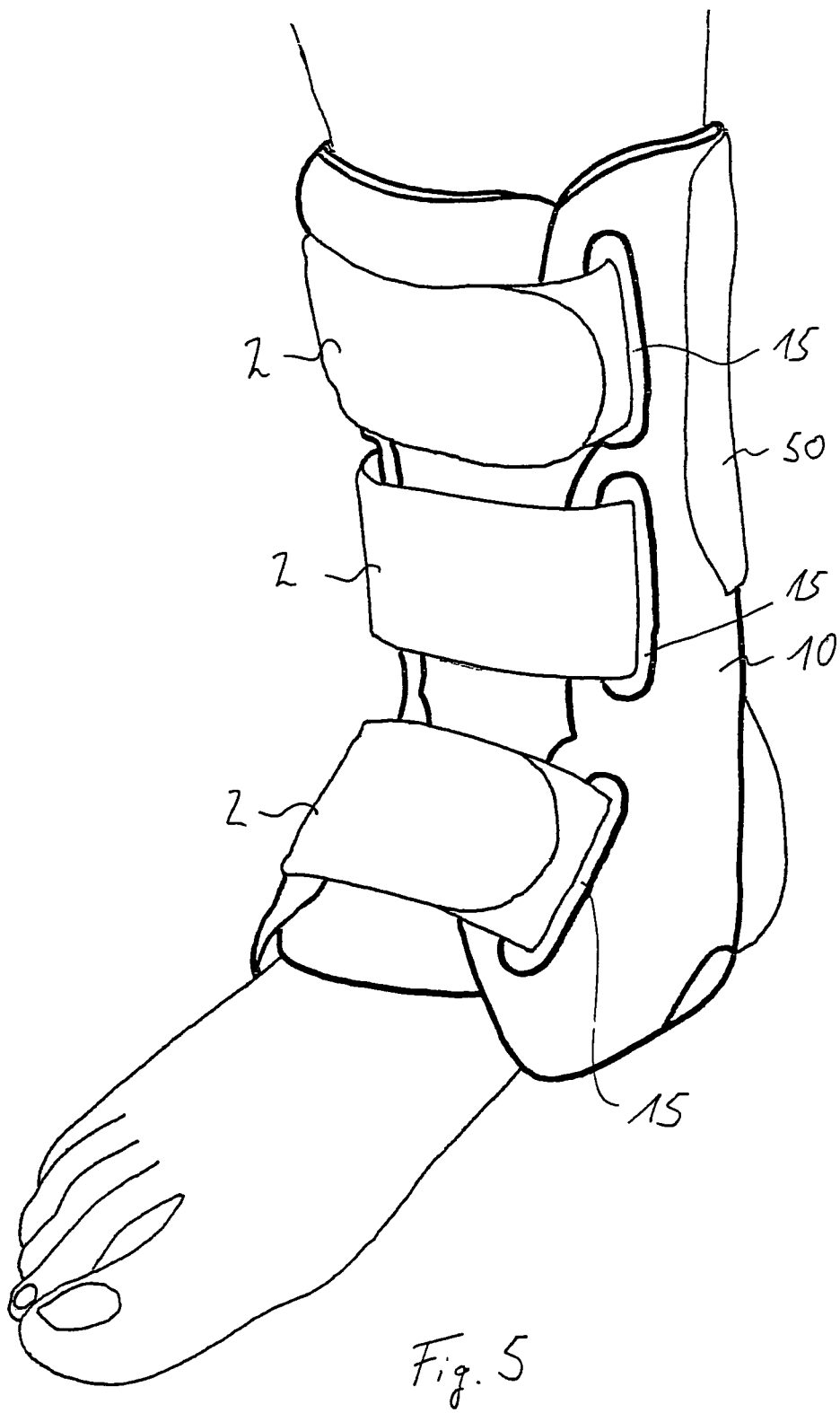
FIGS. 5 and 6 show perspective oblique plan views of an applied base body without external frame.
Figure 6:
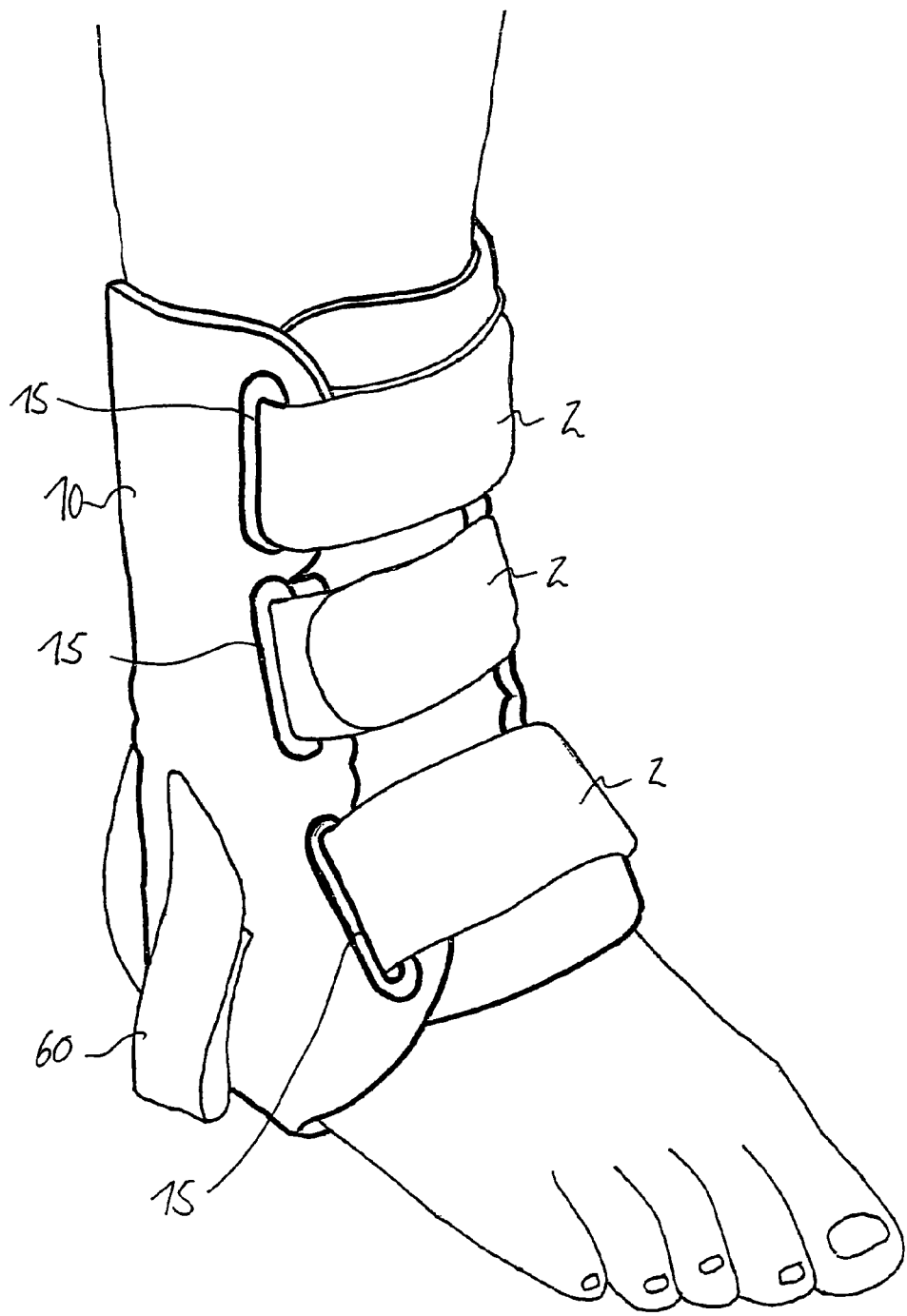

FIGS. 5 and 6 respectively illustrate a perspective oblique planar view of a base body 10 in an applied state as a brace for an ankle joint. The base body 10 is fixed to both the lower leg and the foot by means of locking devices 2 formed as hook straps, and the ankle joint is stabilized thereby. On the medial side, an interlocking element 50 in the form of a receptacle pocket is arranged above the ankle joint on the outside of the base body 10 and an external frame 70 can be inserted therein. The interlocking element 50 is open from below, and so the external frame 70 can be inserted therein from below and this prevents a bending movement of the lower leg relative to the foot when the foot is fixed to said frame. The locking devices 2 are guided within the base body 10 through cuts 15 and can be designed such that their breadth can be adjusted such that the individual circumstances of the wearer of the brace system or the base body 10 can be matched. The base body 10 can be cushioned on all sides and can be provided with a layer of fleece in order to increase the comfort of wear and be able to provide a counter-hold for hook elements of a hook-and-loop fastener. Cushioning is arranged both on the dorsal side of the foot and the frontal side of the shinbone and said cushioning can be fixed to the base body 10 such that the locking devices 2 do not come to rest directly on the skin of the brace system wearer. In addition to the interlocking element 50 being formed as an insert pocket, said element can also have a different shape, for example, it can be formed as a projection, pushbutton, tab, strap, or hook-and-loop fastener.

FIG. 6 illustrates an attachment means 60 in the form of a hook tape on the lateral side, which tape is fixed to the base body 10 at one end, e.g. sewn on, stuck on or welded on, while the other free end is attached to an outside layer of fleece on the base body 10. In order to attach an external frame, the detachable end of the attachment means 60 can be pulled through a cut and then be re-attached to the base body 10 in order to allow an external frame 70 to be fixed in the plantar region in this fashion. Instead of attachment by means of a seam, the hook tape can also be fixed to the base body 10 by means of a hook-and-loop fastener.

Figure 7:
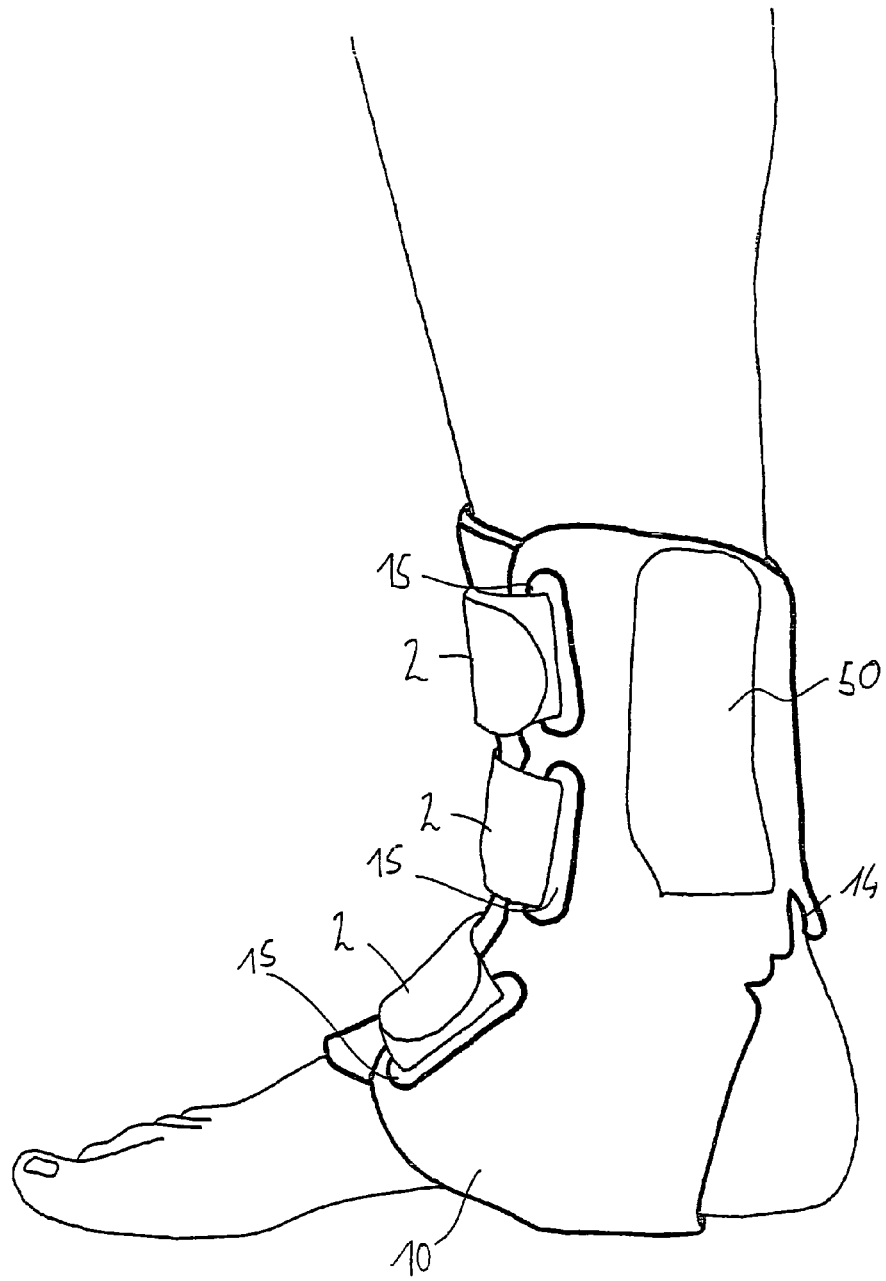
FIGS. 7 and 8 show side views of an applied base body without external frame.
Figure 8:
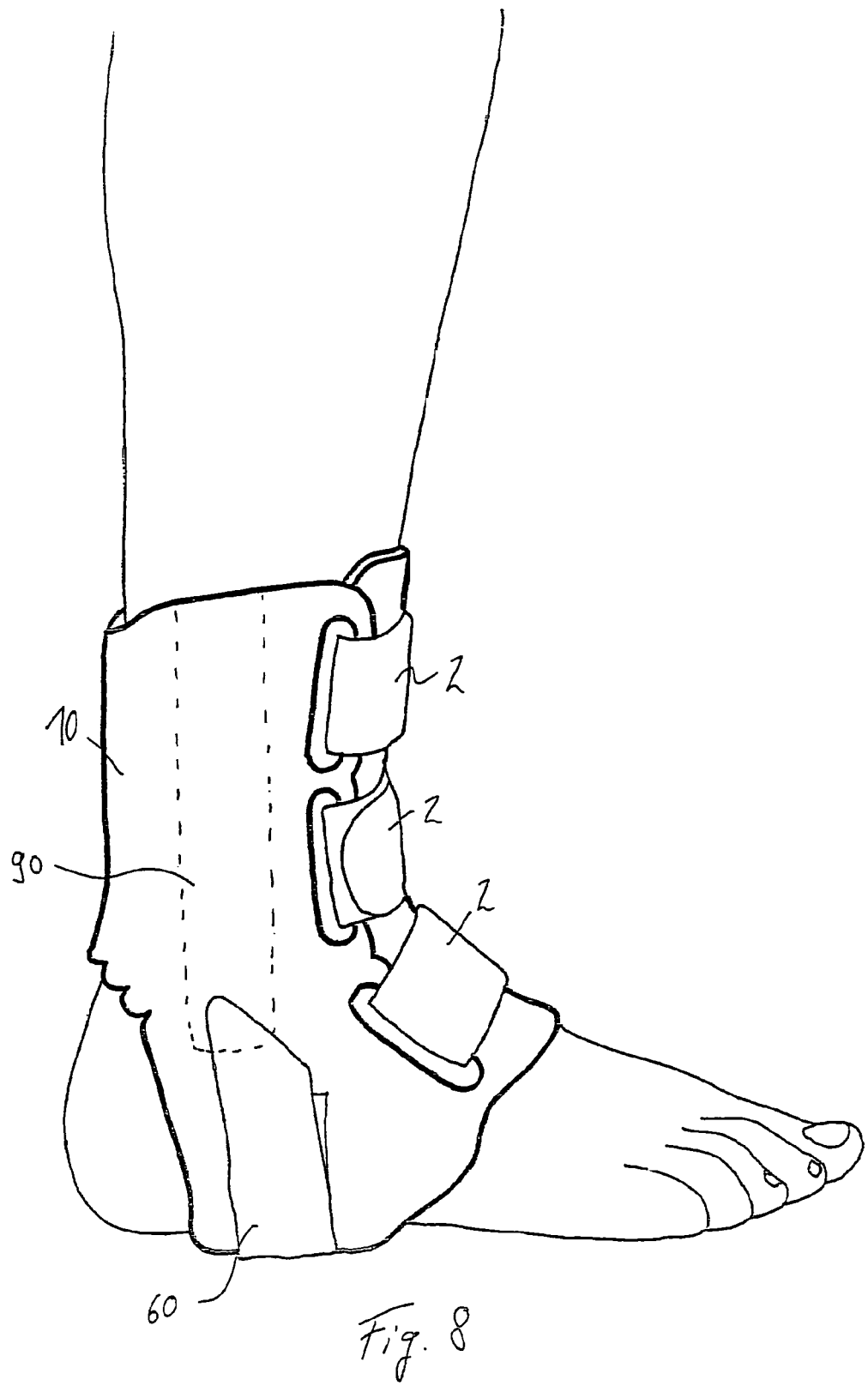

FIGS. 7 and 8 show side views of the applied base body 10, which show, on the one hand, the arrangement of the interlocking element 50 in the form of an insert pocket on the medial side and, on the other hand, the arrangement of a receptacle device 90 for stiffening elements (not illustrated), e.g. splints or the like, on the lateral side. In principle, provision can be made for the base body 10 to have a symmetric design and so it can be used for both the left and the right foot. For this, both the interlocking elements 50 and the receptacle devices 90 for stiffening elements are arranged on both sides, i.e. laterally and medially. This affords the possibility of fixing the foot in both pronation and supination, to the right and to the left, by fixing an appropriate external frame 70 to the base body 10. For this, the attachment means 60 can also be provided both medially and laterally. If the attachment means 60 is fixed to the base body 10 only by means of hook-and-loop fasteners, there is no need for a repeated embodiment. Fixing in the desired pronation with, if need be, dorsal extension can be brought about by means of the attachment means 60, 80 or separate tension belts, which can have an inelastic or semi-elastic design.

The receptacle device 90 for stiffening elements can extend beyond the joint in order to be able to provide an additional stiffening effect. The receptacle device 90 or the receptacle devices 90 is or are preferably designed as pockets, which have for example been worked into the region between an outer layer of fleece and a plastic base material. It is likewise possible for the receptacle devices 90 for stiffening elements to be covered by the interlocking element 50, that is to say that a plurality of pockets are arranged above one another, into which pockets stiffening elements on the one hand and the external frame on the other hand can be inserted. The receptacle devices 90 for the stiffening elements can be closed off and so the stiffening elements, in particular stiffening splints, cannot be inadvertently pushed out of the receptacle devices 90.

Figure 9:
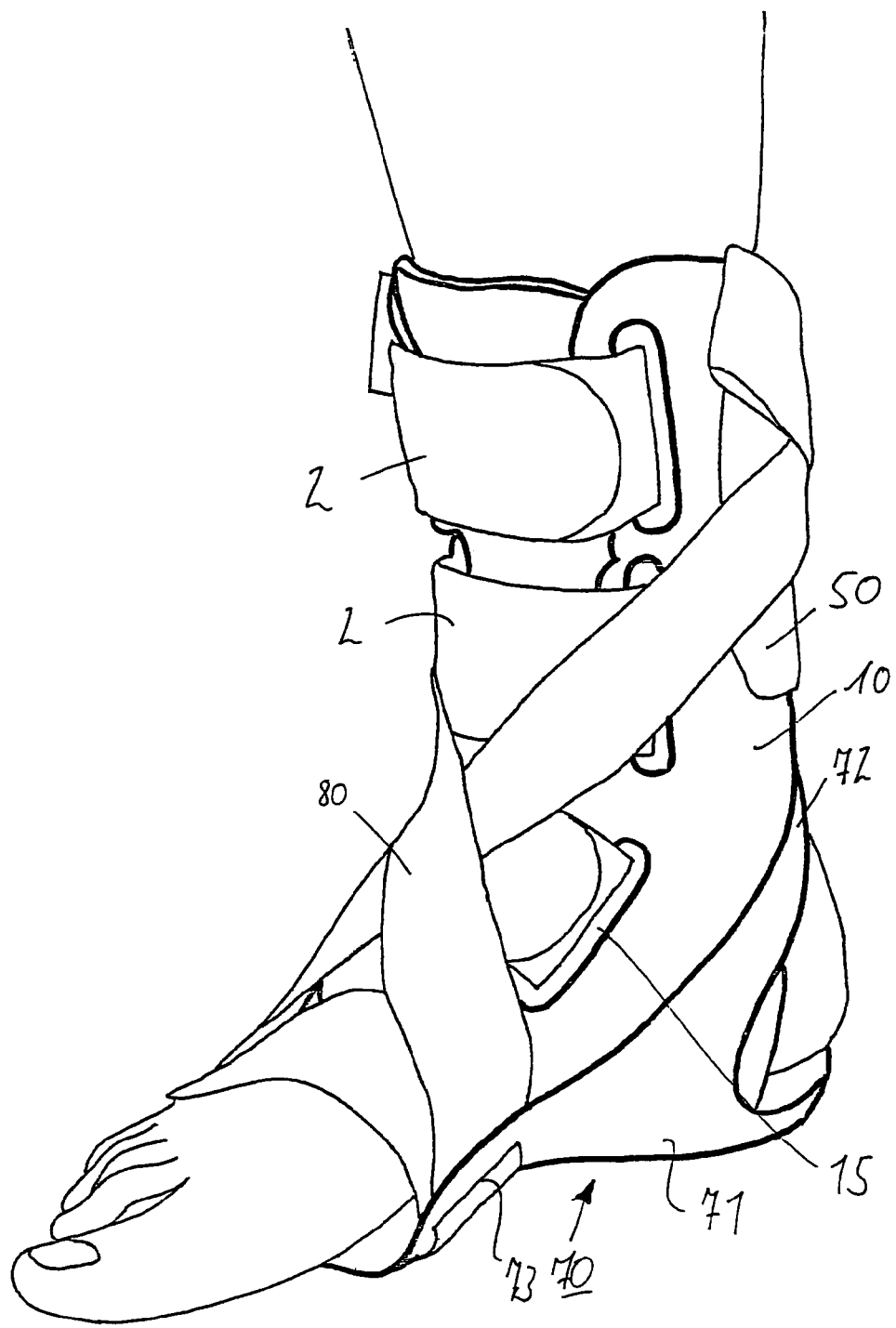
FIGS. 9 and 10 show perspective oblique plan views of an applied base body with an external frame.
Figure 10:
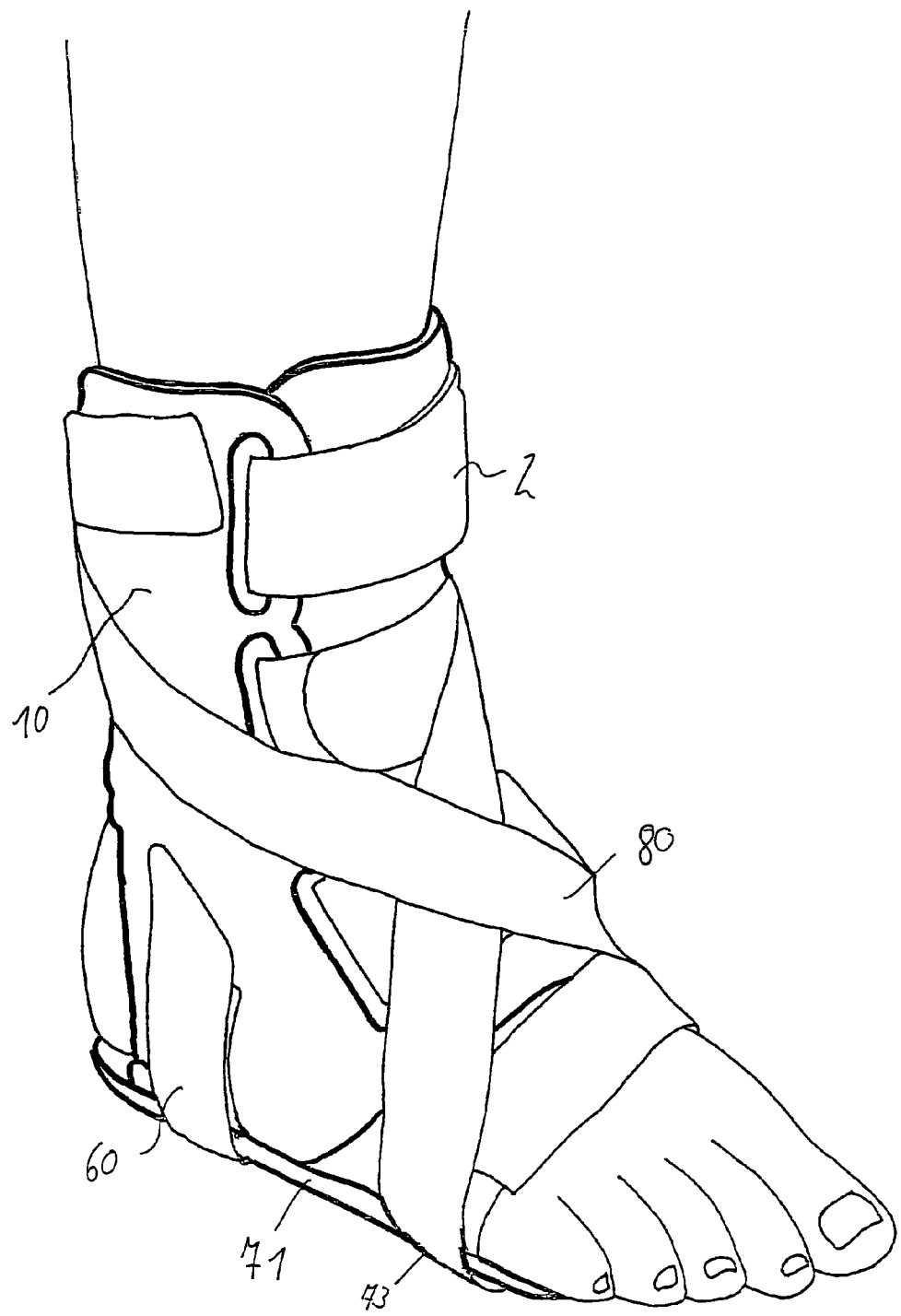

FIGS. 9 and 10 show perspective oblique views of an applied brace system, consisting of a base body 10 and an external frame 70 fixed thereto, which are fixed to one another by means of attachment means 80, 60 in the form of hook-and-loop-fastener tapes. Here, the external frame 70 has an integral design and has a plantar region 71 and a lower leg region 72. The lower leg region 72 is inserted into the interlocking element 50 in the form of an insert pocket. The attachment means 80 in the form of a flexible, inelastic hook tape is guided through slits 73 in the plantar region 71 of the external frame 70 and is then guided along the upper side of the foot in a crisscross fashion in order then to be fixed to the outside of the base body 10 in the region of the lower leg. The crisscross guiding of the attachment means 80 over the back of the foot, the medial and lateral arrangement on the external frame 70, and the full-surface abutment due to the layer of fleece on the outside of the base body 10 and on the outside of the interlocking element 50 allow extensive stabilization of the ankle joint and the immobilization thereof. The attachment means 80 can additionally be fixed in the region of the calves of the base body 10. FIG. 10 indicates that the second attachment means 60 is likewise guided along through slits (not illustrated) and fixes the second part 71 of the external frame 70 to the base body 10 in the ankle region. By way of example, this can keep the foot in the desired position, in pronation or in supination.

Figure 11:
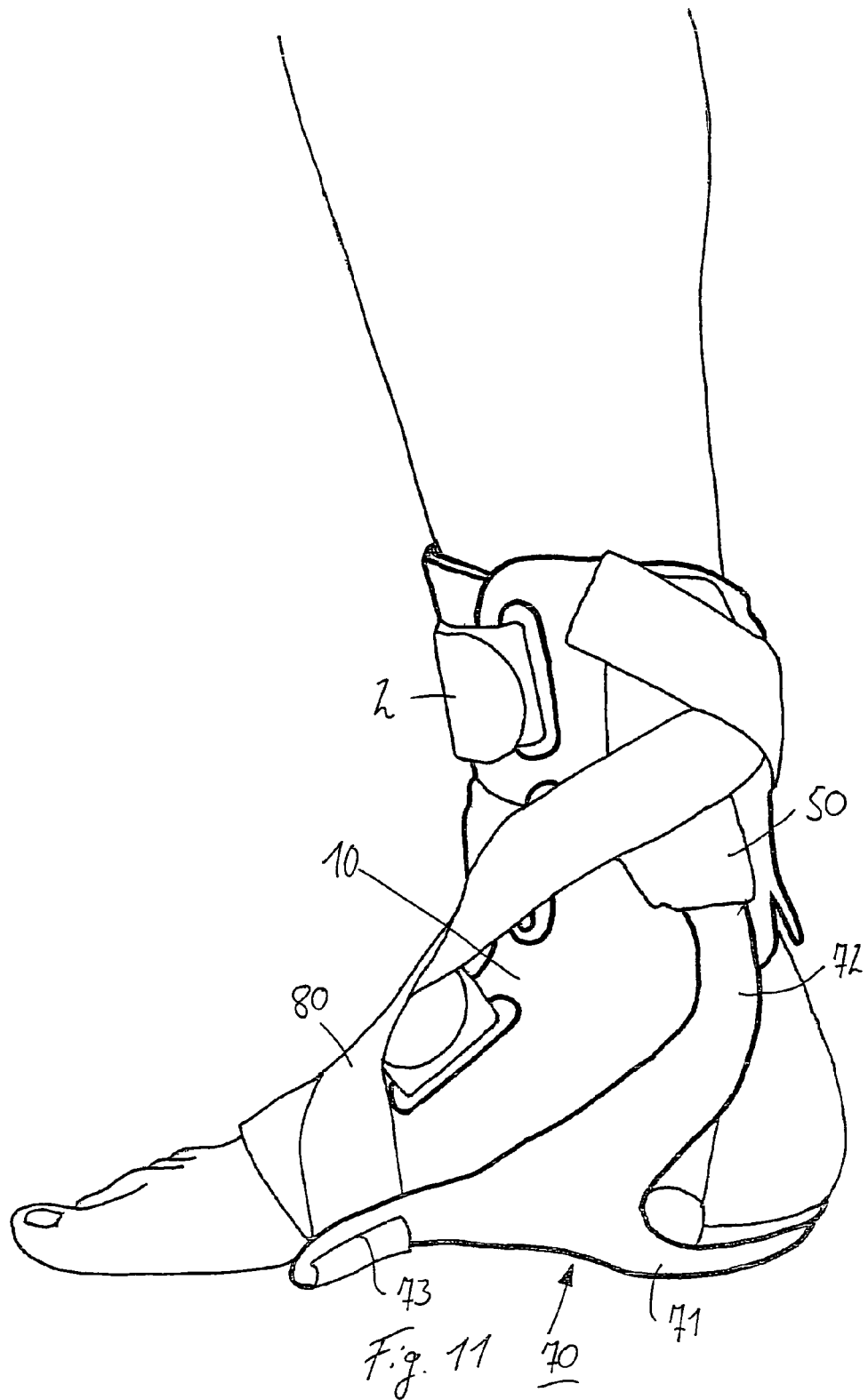
FIGS. 11 and 12 show side views of an applied base body with an external frame.
Figure 12:
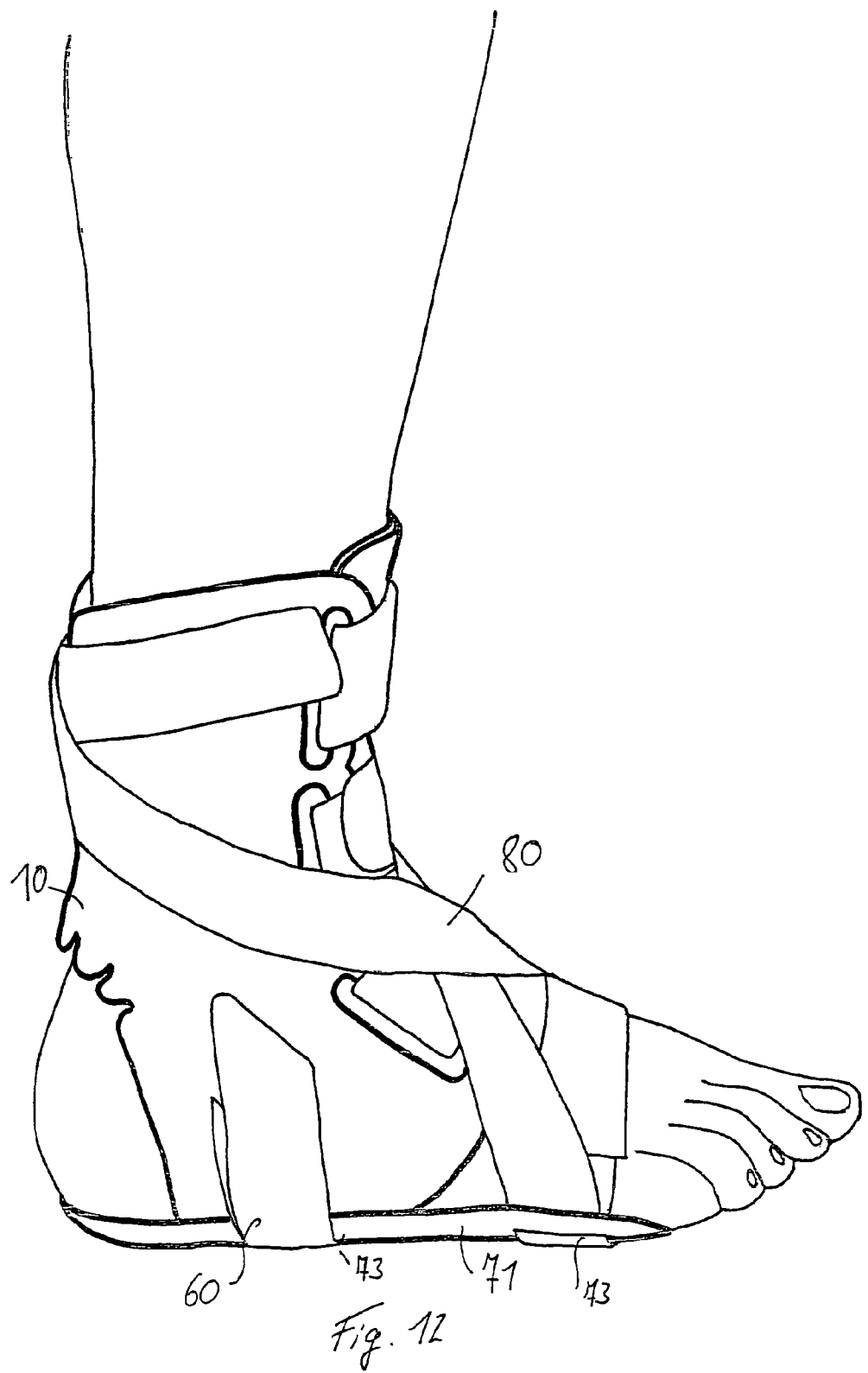

FIGS. 11 and 12 show the arrangement of the attachment means 60, 80 and the fixing of the external frame 70, in particular of the first part 72 assigned to the lower leg in the interlocking element 50. The external frame 70 has an integral design and it is curved such that the first part 72 extends behind the ankle in the direction of walking in order to be able to provide wear that is as comfortable as possible. By inserting the first part 72 into the pocket 50 and fixing it by means of the attachment means 60, 80, the brace system comprising base body 10, external frame 70 and, if need be, stiffening elements can easily be matched to the therapeutic requirements.

Figure 13:
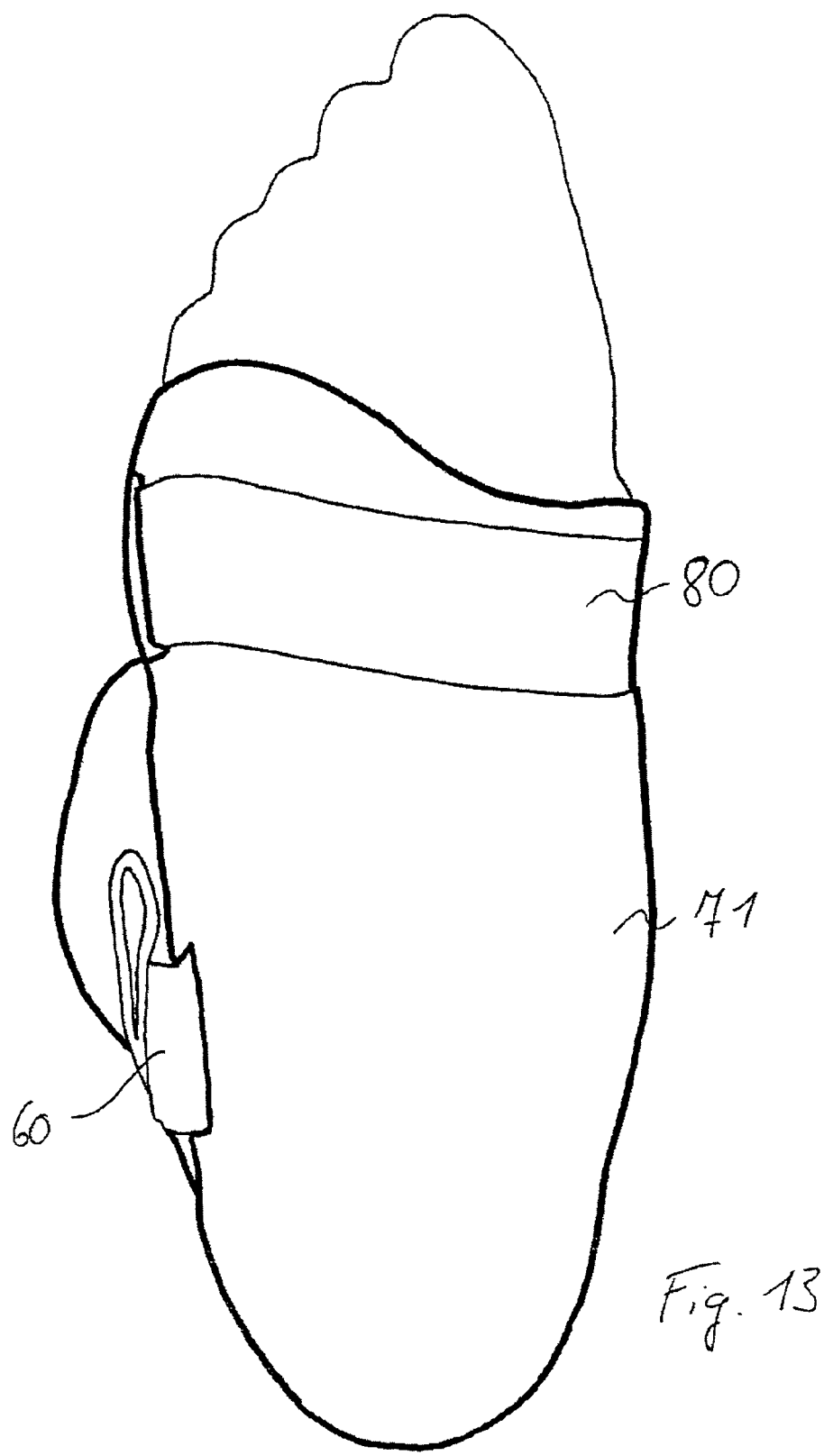
FIG. 13 shows a bottom view with an external frame.

FIG. 13 shows a bottom view of the applied brace system, in which the plantar part 71 of the external frame 70 can be seen. The attachment means 80 is guided along below the stiff foot shell and so the foot is held in the foot shell due to guiding of the attachment means 80 such that it crosses over the top of the foot. In the present case, the second attachment means 60 can be used to implement a pronation of the foot by correspondingly fixing the foot shell 71 to the base body 10. The orthopedic brace system as illustrated thus consists of a relatively flexible base body 10, preferably with integrated stiffening elements, an external frame 70 and attachment means 60, 80 that, in the form of a bandage, afford a combination of base body 10 and external frame 70. This banding by means of the attachment means 60, 80 leads to further stabilization of the joint.

Hence, the system is an orthesis that can be rigged or stripped down with at least one inherently stable, elastic insert in the form of a base body 10 and an external frame 70 and, if need be, additional stiffening elements.

We claim:

1. An orthotic system for an ankle joint, comprising:
    an inherently stable, flexible base body configured to be placed around limbs adjoining the ankle joint, the base body comprising:
        locking devices configured to fix the base body against the limbs adjoining the ankle joint;
        at least one interlocking element arranged on an outside of the base body, the at least one interlocking element comprising a pocket;
        at least one stiffening element configured to stiffen the base body to provide support to the ankle joint;
    an inherently stable, stiff external frame configured to extend over and immobilize the ankle joint, the external frame being fixed to the base body in a detachable fashion using at least one adjustable attachment member, the external frame being configured to be supported by the limbs adjoining the ankle joint, the external frame having a single-piece construction that comprises:
        a planar portion configured to extend along a bottom surface of a foot that adjoins the ankle joint from a heel portion to at least a mid-foot portion of the foot;
        a vertical portion extending from the planar portion and configured to extend along a medial side of the ankle joint, the vertical portion being configured to terminate vertically above the ankle joint along a lower leg that adjoins the ankle joint;
    wherein the at least one interlocking element is fixed to at least one part of the external frame, and the at least one stiffening element provides support to the ankle joint independent of the external frame.

2. The orthotic system for an ankle joint as claimed in claim 1, wherein the interlocking element is sewn on, stuck on, attached by a hook-and-loop fastener or welded on.

3. The orthotic system for an ankle joint as claimed in claim 1, wherein the external frame is mounted in the interlocking element such that the external frame can be displaced in a longitudinal direction.

4. The orthotic system for an ankle joint as claimed in claim 1, wherein the at least one adjustable attachment member comprises hook-and-loop fasteners.

5. The orthotic system for an ankle joint as claimed in claim 1, wherein receptacle devices to receive the at least one stiffening element is formed on or in the base body.

6. The orthotic system for an ankle joint as claimed in claim 5, wherein the receptacle devices comprise pockets.

7. The orthotic system for an ankle joint as claimed in claim 5, wherein the stiffening elements are arranged to limit at least one movement direction of the ankle joint.

8. The orthotic system for an ankle joint as claimed in claim 1, wherein the external frame is made from plastics, composite materials or light metal.

9. The orthotic system for an ankle joint as claimed in claim 1, wherein a first part of the external frame is configured to extend along a lower leg and a second part of the external frame is configured to extend in a plantar region of a foot.

10. The orthotic system for an ankle joint as claimed in claim 9, wherein the first part and the second part are arranged at a substantially right angle with respect to one another.

11. The orthotic system for an ankle joint as claimed in claim 9, wherein the second part can be bent into a pronation and/or dorsal extension with respect to the first part.

12. The orthotic system for an ankle joint as claimed in claim 9, wherein the second part is configured to not cover a first metatarsal head of the foot.

13. The orthotic system for an ankle joint as claimed in claim 9, wherein a plantar region of the base body is formed by two mutually opposing base-body sections, which are coupled to one another with at least one connection element, which has hook elements.

14. The orthotic system for an ankle joint as claimed in claim 13, wherein the connection element comprises a double-sided hook blank.

15. The orthotic system for an ankle joint as claimed in claim 13, wherein the at least one connection element is a separate blank.

16. The orthotic system for an ankle joint as claimed in claim 1, wherein incisions are introduced in the base body in the region of the Achilles tendon, with adjustment wings being formed by the incisions.

17. The orthotic system for an ankle joint as claimed in claim 1, wherein the locking devices comprise hook elements.

18. The orthotic system for an ankle joint as claimed in claim 17, wherein the locking devices comprise micro-hook elements.

19. The orthotic system for an ankle joint as claimed in claim 17, wherein the external frame is configured to extend along only a medial side of the ankle joint.

20. The orthotic system for an ankle joint as claimed in claim 1, wherein the locking devices are attached to the base body, formed in particular as belts, and are sewn into through-holes of the base body whilst forming a loop.

21. The orthotic system for an ankle joint as claimed in claim 1, wherein the base body has cushioning in the form of a layer of fleece.

22. The orthotic system for an ankle joint as claimed in claim 21, wherein the cushioning is at least one of bonded and welded onto the base body.

23. The orthotic system for an ankle joint as claimed in claim 21, wherein the layer of fleece is bonded or welded to the base body.

24. The orthotic system for an ankle joint as claimed in claim 1, wherein the base body is completely coated by a layer of fleece on an outside surface of the base body.

25. The orthotic system for an ankle joint as claimed in claim 1, wherein the base body has cuts within its contour.

26. The orthotic system for an ankle joint as claimed in claim 25, wherein the cuts have been introduced into the base body in a primary forming method or by a separation method.

27. The orthotic system for an ankle joint as claimed in claim 25, wherein the base body includes a layer of fleece and cushioning which are welded or bonded to one another through the cuts.

28. The orthotic system for an ankle joint as claimed in claim 1, wherein the base body has a multi-layered design.

29. The orthotic system for an ankle joint as claimed in claim 1, wherein the base body has a mirror-symmetric design.

30. The orthotic system for an ankle joint as claimed in claim 1, wherein material weakening are formed in the base body along folding or bending lines.

31. The orthotic system for an ankle joint as claimed in claim 1, wherein the base body includes a layer of fleece, and a fixing belt is attached to the layer of fleece with hook elements.

32. The orthotic system for an ankle joint as claimed in claim 1, wherein the at least one adjustable attachment member comprises an inelastic or semi-elastic tension belt, which can be fixed to the base body.

33. An orthotic system for an ankle joint, comprising:
a flexible base body configured to be placed around limbs adjoining the ankle joint, the flexible base body having a stiffening portion to stiffen the base body;
at least one locking device configured to fix the base body to the limbs adjoining the ankle joint;
a stiff external frame configured to extend over and immobilize the ankle joint and being supported by the limbs adjoining the ankle joint;
a single-piece adjustable attachment member configured to detachably connect the external frame to the base body, the adjustable member being connected to a distal end of the base body and having free ends configured to cross each other along a top surface of a foot adjoining the ankle joint and wrap around and connect to the base body at a location above the ankle joint;
wherein the base body provides support to the ankle joint independent of the external frame.

34. An orthotic system for an ankle joint, comprising:
an inherently stable, flexible base body configured to be placed around limbs adjoining the ankle joint, the base body comprising:
locking devices configured to fix the base body against the limbs adjoining the ankle joint;
at least one interlocking element arranged on an outside of the base body;
at least one stiffening element configured to stiffen the base body to provide support to the ankle joint;
an inherently stable, stiff external frame configured to extend over and immobilize the ankle joint, the external frame being fixed to the base body in a detachable fashion using at least one adjustable attachment member, the external frame being configured to be supported by the limbs adjoining the ankle joint;
the external frame having a single-piece construction that comprises:
a planar portion configured to extend along a bottom surface of a foot that adjoins the ankle joint from a heel portion to at least a mid-foot portion of the foot;
a vertical portion extending from the planar portion and configured to extend along a medial side of the ankle joint, the vertical portion being configured to terminate vertically above the ankle joint along a lower leg that adjoins the ankle joint;
wherein the at least one interlocking element is fixed to at least one part of the external frame such that the external frame can be displaced in a longitudinal direction, and the at least one stiffening element provides support to the ankle joint independent of the external frame.

35. An orthotic system for an ankle joint, comprising:
an inherently stable, flexible base body configured to be placed around limbs adjoining the ankle joint, the base body comprising:
locking devices configured to fix the base body against the limbs adjoining the ankle joint;
at least one stiffening element configured to stiffen the base body to provide support to the ankle joint;
an inherently stable, stiff external frame configured to extend over and immobilize the ankle joint is fixed to the base body in a detachable fashion using at least one adjustable attachment member, the external frame being configured to be supported by the limbs adjoining the ankle joint, the external frame having a single-piece construction that comprises:

a planar portion configured to extend along a bottom surface of a foot that adjoins the ankle joint from a heel portion to at least a mid-foot portion of the foot;

a vertical portion extending from the planar portion and configured to extend along a medial side of the ankle joint, the vertical portion being configured to terminate vertically above the ankle joint along a lower leg that adjoins the ankle joint;

a first part of the external frame configured to extend along a lower leg;

a second part of the external frame configured to extend in a plantar region of a foot, wherein the second part is configured to not cover a first metatarsal head of the foot;

wherein the at least one stiffening element provides support to the ankle joint independent of the external frame.

36. An orthotic system for an ankle joint, comprising:

an inherently stable, flexible base body configured to be placed around limbs adjoining the ankle joint, the base body comprising:
- locking devices configured to fix the base body against the limbs adjoining the ankle joint;
- at least one stiffening element configured to stiffen the base body to provide support to the ankle joint;
- a plantar region formed by two mutually opposing base-body sections, which are coupled to one another with at least one connection element, which has hook elements, the hook elements comprising a double-sided hook blank;

an inherently stable, stiff external frame configured to extend over and immobilize the ankle joint is fixed to the base body in a detachable fashion using at least one adjustable attachment member, the external frame being configured to be supported by the limbs adjoining the ankle joint, the external frame having a single-piece construction that comprises:
- a planar portion configured to extend along a bottom surface of a foot that adjoins the ankle joint from a heel portion to at least a mid-foot portion of the foot;
- a vertical portion extending from the planar portion and configured to extend along a medial side of the ankle joint, the vertical portion being configured to terminate vertically above the ankle joint along a lower leg that adjoins the ankle joint;
- a first part of the external frame configured to extend along a lower leg;
- a second part of the external frame configured to extend in a plantar region of a foot;

wherein the at least one stiffening element provides support to the ankle joint independent of the external frame.

\* \* \* \* \*